US012344884B2

(12) United States Patent
Jost et al.

(10) Patent No.: US 12,344,884 B2
(45) Date of Patent: Jul. 1, 2025

(54) SAMPLE PREPARATION METHOD AND SYSTEM

(71) Applicant: GEN-PROBE INCORPORATED, San Diego, CA (US)

(72) Inventors: Matthias Jost, San Diego, CA (US); Barbara L. Eaton, San Diego, CA (US); Ankur Shah, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 662 days.

(21) Appl. No.: 17/255,500

(22) PCT Filed: Jun. 14, 2019

(86) PCT No.: PCT/US2019/037245
§ 371 (c)(1),
(2) Date: Dec. 23, 2020

(87) PCT Pub. No.: WO2020/005584
PCT Pub. Date: Jan. 2, 2020

(65) Prior Publication Data
US 2021/0269854 A1    Sep. 2, 2021

Related U.S. Application Data

(60) Provisional application No. 62/691,478, filed on Jun. 28, 2018.

(51) Int. Cl.
*C12Q 1/6806* (2018.01)
*C12N 15/10* (2006.01)
*C12Q 1/689* (2018.01)

(52) U.S. Cl.
CPC ....... *C12Q 1/6806* (2013.01); *C12N 15/1006* (2013.01); *C12Q 1/689* (2013.01)

(58) Field of Classification Search
CPC .............................. C12Q 1/6804; C12N 15/10
See application file for complete search history.

(56) References Cited

U.S. PATENT DOCUMENTS

| | | | |
|---|---|---|---|
| 4,965,188 A | 10/1990 | Mullis et al. | |
| 5,399,491 A | 3/1995 | Kacian et al. | |
| 5,455,166 A | 10/1995 | Walker | |
| 5,472,840 A | 12/1995 | Stefano | |
| 7,510,837 B2 | 3/2009 | Gao et al. | |
| 8,258,281 B2 | 9/2012 | Vuylsteke et al. | |
| 8,420,317 B2 | 4/2013 | Gao et al. | |
| 2002/0019007 A1* | 2/2002 | Jensen | C12Q 1/689 435/6.12 |
| 2004/0229268 A1 | 11/2004 | Hogan et al. | |
| 2005/0118593 A1 | 6/2005 | Potocki et al. | |
| 2007/0031880 A1* | 2/2007 | Lou | C07H 21/04 536/25.4 |
| 2012/0058011 A1 | 3/2012 | Wirbisky et al. | |
| 2012/0071360 A1* | 3/2012 | Gao | C12Q 1/6806 506/26 |
| 2013/0132006 A1* | 5/2013 | Gwynn | B01L 3/021 702/55 |
| 2014/0205996 A1 | 7/2014 | Lizzi et al. | |
| 2015/0218653 A1 | 8/2015 | Sprenger-Haussels et al. | |
| 2018/0163259 A1 | 6/2018 | Peterson et al. | |

FOREIGN PATENT DOCUMENTS

| | | |
|---|---|---|
| CA | 2679843 C | 10/2018 |
| EP | 0135159 A2 | 3/1985 |
| EP | 0270017 A2 | 6/1988 |
| EP | 0525882 B1 | 1/2004 |
| JP | 2006-517225 A | 7/2006 |
| JP | 2014-045689 A | 7/2006 |
| WO | 2004072229 A2 | 8/2004 |
| WO | WO 2006/073497 A1 | 7/2006 |
| WO | WO 2011/083076 A1 | 7/2011 |
| WO | WO 2014/144174 A1 | 9/2014 |
| WO | WO 2017/088169 A1 | 6/2017 |

OTHER PUBLICATIONS

Belgrader et al., BioTechniques 19(3): 426-432 (Year: 1995).*
Merel et al.Clinical Chemistry42(8) : 1285 (Year: 1996).*
Mischiati et al., BioTechniques 15(1) :146 (Year: 1993).*
PCT International Search Report and Written Opinion, International Application No. PCT/US2019/037245, Sep. 3, 2019.
PCT International Preliminary Report on Patentability, International Application No. PCT/US2019/037245, Dec. 29, 2020.
EPO Communication pursuant to Article 94(3) EPC, European Application No. 19734637.2, Jan. 31, 2022.
JPO Official Action, Japanese Patent Application No., 2020-572965, Jan. 17, 2024.
JPO Official Action, Japanese Patent Application No., 2020-572965, Jun. 15, 2023.
Lizardi et al., BioTechnology 6:1197 (1988).
Birnboim and Doly, "A rapid alkaline extraction procedure for screening recombinant plasmid DNA", (1979) Nucleic Acids Res 7(6), pp. 1513-1523.
Brown and Audet, "Current techniques for single-cell lysis", (2008) J R Soc. Interface 5: S131-S138.
Brown et al. "Chemistry: The Central Science", 12th ed. (2012) Pearson Education, Inc., Section 4.3, p. 125.

(Continued)

*Primary Examiner* — Ethan C Whisenant
(74) *Attorney, Agent, or Firm* — Michael J. Gilly

(57) ABSTRACT

Method of preparing a biological sample appropriate for use in a subsequent in vitro nucleic acid amplification reaction. A biological sample is combined with an alkaline composition that lyses cells and denatures DNA to create a first liquid composition. The first liquid composition is then mixed with a buffer, a detergent, and a solid support that captures DNA to create a second liquid composition. The buffer, detergent, and solid support can be delivered as components of a single reagent. Captured DNA strands can be used as templates in subsequently performed nucleic acid amplification and detection reactions with improved sensitivity.

20 Claims, No Drawings

(56) References Cited

OTHER PUBLICATIONS

Brown et al. "Chemistry: The Central Science", 12th ed. (2012) Pearson Education, Inc., Section 16.5, pp. 664-666.

Chomczynski and Rymaszewski, "Alkaline Polyethylene Glycol-Based Method for Direct PCR from Bacteria, Eukaryotic Tissue Samples, and Whole Blood", (2006) BioTechniques, 40(4), pp. 454-458.

Darnell et al., "Whole mount in situ hybridization detection of mRNAs using short LNA containing DNA oligonucleotide probes", (2010) RNA, 16(3): pp. 632-637.

Handbook Invitrogen user guide "Dynabeads® DNA DIRECT™ Universal for the Isolation of PCR-Ready Genomic DNA From Small Samples", from Life Technologies, Catalog No. 63006, (2012) pp. 1-36.

Handbook Invitrogen user guide "Purelink™ HiPure Plasmid DNA Purification Kits for mini, midi and maxi preparation of plasmid DNA", from Thermo Fischer Scientific, Catalog No. K2100-02-K2100-07, Revision B.0, Publication No. MAN0000486, (2015) pp. 1-46.

Islam et al. "A Review on Mascroscale and Microscale Cell Lysis Methods", (2017) Micromachines, 8: 83, pp. 1-27.

Klintschar and Neuhuber, "Evaluation of an Alkaline Lysis Method for the Extraction of DNA from Whole Blood and Forensic Stains for STR Analysis", (2000) ASTM International J Forensic Sci, 45(3), pp. 669-673.

Machine translation of JP 2014-045689 A, 28 pages.

Merel et al. "Completely Automated Extraction of DNA from Whole Blood", (1996) Clin Chem., 42(8), pp. 1285-1286.

Nelson and Cox, "Lehninger: Principles of Biochemistry", 4th ed. (2004) W.H. Freeman, pp. 291, 314, and 315.

Notice of Opposition to a European Patent, for European Patent No. EP3814496, submitted Aug. 22, 2024, 44 pages.

Response to Examination Report during examination of the Opposed Patent dated May 25, 2022, 7 pages.

Rudbeck and Dissing, "Rapid, Simple Alkaline Extraction of Human Genomic DNA from Whole Blood, Buccal Epithelial Cells, Semen and Forensic Stains for PCR", (1998) BioTechniques, 25(4), pp. 588-592.

Schrader et al. "PCR inhibitors—occurrence, properties and removal", (2012) J Appl Microbiol, 113(5), pp. 1014-1026.

Truett et al. "Preparation of PCR-Quality Mouse Genomic DNA with Hot Sodium Hydroxide and Tris (HotSHOT)", (2000) BioTechniques, 29(1), pp. 52-54.

Examination Report issued Oct. 23, 2024, in counterpart Australian Application No. 2019294109.

Response to Opposition filed Jan. 3, 2025, in counterpart European Application No. 19734637.2.

Notice of Reasons for Rejection issued May 13, 2024, in counterpart Japanese Application No. 2020-572965.

\* cited by examiner

SAMPLE PREPARATION METHOD AND SYSTEM

RELATED APPLICATIONS

This application is a national phase entry pursuant to 35 U.S.C. § 371 of International Application No. PCT/US2019/037245, filed Jun. 14, 2019, which claims the benefit of U.S. Provisional Application No. 62/691,487, filed Jun. 28, 2018. The entire disclosures of these prior applications are hereby incorporated by reference.

FIELD

The present disclosure relates to the field of nucleic acid isolation. More specifically, the disclosure relates to a method of preparing DNA from a biological sample. Still more specifically, the disclosure relates to automated methods and systems for isolating DNA from a biological sample, and then amplifying the isolated DNA.

BACKGROUND

In vitro nucleic acid amplification techniques are now commonly used for synthesizing and detecting vanishingly small quantities of a nucleic acid target. These techniques conventionally employ one or more oligonucleotide primers and a nucleic acid-polymerizing enzyme to synthesize copies of one or both strands of a nucleic acid template. Many different methods have been used for preparing biological samples in advance of the amplification procedure.

Differences in the efficiencies of sample preparation techniques present challenges to diagnostic assays that detect amplified nucleic acids. The fact that a single technique lyses different organisms to cause release of nucleic acids with different efficiencies means that specialized techniques may be required for processing different organisms. U.S. Pat. No. 8,420,317 details the "alkaline shock" sample preparation technique that can be used for isolating both RNA and DNA from a wide range of organisms, including many organisms that are difficult to lyse. Methods employing detergents, or the combination of detergent and alkali represent alternative approaches for isolating amplifiable nucleic acids, for example from bacterial organisms preliminary to in vitro amplification.

Automated systems frequently are employed for preparing nucleic acids from biological samples, and can streamline laboratory workflows by further conducting the nucleic acid amplification and detection step. Here the number and type of onboard reagents can be critical limitations when working with assays that are not packaged or configured as individual tests. In other words, the number and type of reagents available for performing the sample preparation step may constrain the range of sample preparation methods that can be practiced. The usefulness of automated sample processing instruments would therefore be limited without adding to the collection of onboard reagents.

Accordingly, there is a need for a technique that can enhance the efficiency of nucleic acid isolation, and so detectability of particular targets in nucleic acid amplification reactions. There is a further need for enhancing detectability of one or more targets in multiplex amplification reactions without substantially sacrificing detectability of other targets in the same reaction. The disclosed technique addresses these needs.

Indeed, the technique disclosed herein provides a convenient method for preparing biological samples to be tested for the presence of nucleic acid targets using in vitro nucleic acid amplification. This method advantageously provides reliable DNA isolation results, even with organisms that are difficult to lyse, while dramatically improving detectability of certain nucleic acid targets.

SUMMARY

In one aspect, the disclosure concerns a method of processing a biological sample. Generally speaking, the method includes the steps of: (a) mixing the biological sample with an alkaline composition that lyses cells and denatures DNA to create a first liquid composition, where the first liquid composition has a pH in the range of from about pH 12.0 to about pH 13.5; (b) mixing the first liquid composition with a pH buffered detergent reagent to create a second liquid composition having a pH lower than about pH 9.5, where the pH buffered detergent reagent includes a pH buffer, a detergent, and a solid support particle that captures DNA; and (c) isolating the solid support particle, and any DNA captured thereon, from the second liquid composition.

In some embodiments, the first liquid composition can be substantially free of detergents.

In some embodiments, the biological sample includes viable bacterial cells, and the method can further include the step of culturing the viable bacterial cells to increase the number of bacterial cells.

In some embodiments, the second liquid composition can have a pH in the range of from about pH 8.0 to about pH 9.2.

In some embodiments, each of steps (a)-(c) is conducted onboard an automated instrument that includes a robotic fluid transfer device.

In some embodiments, the method further includes the step of (d) performing an in vitro nucleic acid amplification reaction using DNA isolated in step (c) as templates, and detecting products of the in vitro nucleic acid amplification reaction. For example, detecting products of the in vitro nucleic acid amplification reaction can be used to indicate the presence of a species of Gram-positive bacteria in the biological sample.

In some embodiments, step (d) is also carried out onboard the automated instrument.

In some embodiments, particularly those employing the automated instrument that includes the robotic fluid transfer device, step (a) includes combining the biological sample and the alkaline composition in a reaction vessel to create the first liquid composition, step (b) includes adding the pH buffered detergent reagent to the reaction vessel containing the first liquid composition to create the second liquid composition, and each of steps (a) and (b) is performed using the robotic fluid transfer device of the automated instrument.

In some embodiments, again particularly those employing the automated instrument that includes the robotic fluid transfer device, the automated instrument further includes a transport mechanism that moves the reaction vessel from one position within the automated instrument to a different position within the automated instrument.

In some embodiments, after step (b) and before step (c) there is the step of incubating the first liquid composition for a period of time between 1 minute and 10 minutes.

In some embodiments, the incubating step includes heating the first liquid composition.

In some embodiments, the incubating step includes transporting the reaction vessel from a first position in the automated instrument to a second position in the automated instrument, and the second position in the automated instrument is at a temperature higher than the temperature at the first position in the automated instrument.

In some embodiments, the solid support particle includes a magnetically attractable particle.

In some embodiments, the solid support particle in step (b) is a solid support particle that captures DNA independent of base sequence, and step (c) includes washing the solid support particle to remove any material not immobilized thereon, and then retaining the solid support particle after washing, whereby captured DNA is isolated.

In some embodiments, the alkaline composition includes a strong base in aqueous solution at a concentration of from about 0.1 N to about 2.2 N.

In some embodiments, the pH of the first liquid composition is in the range of from about pH 12.5 to about pH 13.2.

In some embodiments, the pH of the second liquid composition is in the range of from about pH 7.6 to about pH 8.8.

In some embodiments, the alkaline composition includes the strong base at a concentration of from about 1.0 N to about 1.7 N.

In some embodiments, the strong base is any of NaOH, KOH, and LiOH.

In some embodiments, all steps of the method are carried out under automated process control.

Definitions

The following terms have the following meanings for the purpose of this disclosure, unless expressly stated to the contrary herein.

As used herein, a "biological sample" is any tissue or polynucleotide-containing material obtained from a human, animal or environmental sample. Biological samples in accordance with the disclosed technique include peripheral blood, plasma, serum or other body fluid, bone marrow or other organ, biopsy tissues, clinical or screening swabs (e.g., nasal swabs), or other materials of biological origin. Biological samples can be contained in a liquid transport medium for ease of transport and processing. Example biological samples include or contain bacteria, such as Gram-positive bacteria.

As used herein, an "alkaline composition" is an aqueous solution comprising a strong base. Strong bases can ionize or dissociate completely in solution to yield hydroxide ions. Commonly, strong bases are formed from the hydroxides of alkali metals or alkaline earth metals. Examples of strong bases include KOH, NaOH, and LiOH.

As used herein, a "first liquid composition" that results from mixing a biological sample with an alkaline composition is said to be "substantially free of detergents" when the detergent concentration is less than 0.001% (w/v). This allows for the presence of trace amounts of detergent in the first liquid composition, as might be carried in from a prior sample transporting or processing step.

As used herein, "alkaline shock" refers to a transient high pH effected by first combining a biological sample with a pH buffer and a detergent to result in a first composition, and then mixing with that first composition an amount of an alkaline composition.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the disclosed technique can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous assay" refers to a detection procedure that does not require physical separation of hybridized probe from non-hybridized probe prior to determining the extent of specific probe hybridization.

As used herein, "nucleic acid amplification," or simply "amplification" refers to an in vitro procedure for obtaining multiple copies of a target nucleic acid sequence, its complement or fragments thereof.

By "target nucleic acid" or "target" is meant a nucleic acid containing a target nucleic acid sequence. Optionally, a target nucleic acid sequence that is to be amplified will be positioned between two oppositely disposed amplification oligonucleotides, and will include the portion of the target nucleic acid that is fully complementary to each of the amplification oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto. As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present technique fall in a size range of about 10 to about 100 residues. Oligonucleotides may be purified from naturally occurring sources, but preferably are synthesized using any of a variety of well-known enzymatic or chemical methods.

As used herein, the term "probe" refers to an oligonucleotide that interacts with a target nucleic acid to form a detectable complex. A probe optionally may contain a detectable moiety which either may be attached to the end(s) of the probe or may be internal. The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. Particular examples of probes include invasive probes and primary probes, as disclosed in the published patent application identified as U.S. 2018/0163259 A1, the entire disclosure of this application being incorporated by reference.

By "amplification oligonucleotide" is meant an oligonucleotide that is capable of participating in a nucleic acid amplification reaction to bring about the synthesis of multiple copies of a template nucleic acid sequence, or its complement. It is common for amplification reactions to employ at least two amplification oligonucleotides, with at least one of the amplification oligonucleotides serving as an amplification primer.

As used herein, an "amplification primer," or more simply "primer," is an oligonucleotide that hybridizes to a target nucleic acid, or its complement, and can be extended in a template-dependent primer extension reaction. For example, amplification primers may be optionally modified oligonucleotides which are capable of hybridizing to a template nucleic acid, and which have a 3' end that can be extended by a DNA polymerase activity. In general, a primer will have a downstream target-complementary sequence, and optionally an upstream sequence that is not complementary to target nucleic acids. The optional upstream sequence may, for example, serve as an RNA polymerase promoter or contain restriction endonuclease cleavage sites.

By "target capture" or simply "capture" is meant a general process for capturing a polynucleotide from the solution phase onto a solid support. Optionally, target capture can be mediated by formation of a hybrid duplex between a target nucleic acid from solution and a oligonucleotide bound directly or indirectly to a solid support, such as a bead (e.g., a microbead) or particle (e.g., a microparticle). For simplicity, "particle" is used herein when generally referring to beads, microbeads, and microparticles.

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized oligonucleotide" or "immobilized nucleic acid," and variants thereof, is meant a nucleic acid that joins, directly or indirectly, a capture oligonucleotide to an immobilized support. An immobilized probe is an oligonucleotide joined to a solid support that facilitates separation of bound target sequence from unbound material in a sample. An "immobilizable" oligonucleotide is an oligonucleotide that can, by way of complementary base interactions with an oligonucleotide immobilized directly to a solid support, become immobilized to the solid support.

By "separating" or "purifying" or "isolating" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample. The disclosed method permits DNA to be isolated from a biological sample after performing certain processing steps.

As used herein, a "multiplex" assay is a type of assay that measures multiple analytes (two or more) in a single run of the assay.

By "consisting essentially of" is meant that additional component(s), composition(s) or method step(s) that do not materially change the basic and novel characteristics of the present approach may be included in the compositions or kits or methods described herein. Such characteristics include the ability to selectively detect target nucleic acids in biological samples such as a nasal or other swab harboring bacteria. Any component(s), composition(s), or method step(s) that have a material effect on the basic and novel characteristics of the present disclosure would fall outside of this term.

DETAILED DESCRIPTION OF THE PREFERRED EMBODIMENTS

Disclosed herein is a method of isolating DNA from biological samples. The method can be used to isolate DNA from viral, bacterial or eukaryotic sources, and can enhance the sensitivity of amplification-based assays conducted using the isolated nucleic acids as templates. Advantageously, the method can be used to isolate DNA from organisms that are otherwise difficult to lyse. Still further, the method can be used to isolate DNA that is substantially free of RNA.

Generally speaking, advantages of the disclosed approach can be realized by combining a biological sample with an aqueous solution of a strong base, where the solution of strong base is substantially free of pH buffers and detergents, and then neutralizing the alkaline combination with a pH buffer in the presence of detergent. Process advantages can also be realized by integrating a target capture step, for example by including target capture reagents (e.g., magnetically attractable beads, optionally including an immobilized polynucleotide) in the reaction mixture at the time the neutralization step is occurring. This is very different from the "alkaline shock" sample preparation technique, described in commonly owned U.S. Pat. No. 7,510,837, which avoids prolonged direct exposure of the biological sample to strong alkaline conditions. As well, the disclosed technique allows for combining or mixing of detergent with the base-treated sample undergoing processing during the pH neutralizing step when target capture also is taking place. As indicated by the evidence presented below, certain advantages of the disclosed technique are not achieved when the order of reagent addition is reversed.

An observation that prompted development of the disclosed technique concerned the reduced sensitivity of an amplified assay for detecting certain types of bacteria that were known to be difficult to lyse. For example, it was discovered that methicillin resistant *Staphylococcus aureus* (MRSA) bacteria lysed inefficiently under certain conditions, and that a prototype PCR assay for detecting MRSA sometimes yielded incorrect results when using nucleic acids from the lysis as templates. This was the case using a sample preparation technique that relied on contacting a biological sample with a pH buffered detergent solution containing target capture reagents to create a first liquid composition, and then mixing the first liquid composition with an alkaline composition (e.g., an aqueous solution containing a strong base) to yield a second liquid composition appropriate for capture or immobilization of released nucleic acids onto a solid support. This "alkaline shock" technique has been described in U.S. Pat. No. 7,510,837, the disclosure of which is incorporated by reference herein. A modified lysis protocol that involved initial treatment of the biological sample with an alkaline detergent solution followed by pH neutralization using a pH buffered reagent gave improved results with detection of *S. aureus* and MRSA, but still did not provide adequate lysis of another target (*C.*

*difficile*). Increasing the concentration of strong base in the alkaline detergent reagent led to changed physical properties that made the reagent undesirable for laboratory use. Because it was desirable to detect the bacterial target nucleic acids with great sensitivity using a general purpose protocol, it was of interest to develop a new technique that could be used to liberate DNA from a broad spectrum of target organisms.

Biological Samples

As indicated above, the term "biological sample" embraces a wide variety of sample types. Of particular interest, however, are bacteria that typically are difficult to lyse. Exemplary bacteria exhibiting this characteristic include Gram-positive bacteria.

Those having an ordinary level of skill in the art will be aware that Gram-positive bacteria characteristically possess a thick peptidoglycan layer in the bacterial cell wall. Peptidoglycan is a polymer of sugars and amino acids that forms a mesh-like layer outside the plasma membrane of most bacteria. The peptidoglycan layer of the cell wall in Gram-positive bacteria is generally more than twice as thick as it is in Gram-negative bacteria. This makes Gram-positive bacteria substantially more resistant to lysis and release of nucleic acids.

While the disclosed sample preparation or processing technique can be used for isolating DNA from a wide variety of organisms, the technique has particular advantages when used for isolating DNA from Gram-positive bacteria. In preferred embodiments, the isolation procedure is conducted onboard an automated sample preparation instrument. Optionally, the automated sample preparation instrument also performs nucleic acid amplification and monitors formation of amplification products. Gram-positive bacteria used for illustrating the utility of the improved sample preparation technique were *Staphylococcus aureus*, *Clostridium difficile*, and *Streptococcus agalactiae* (a Group B *Streptococcus*).

Preferred pH Buffers and pH Ranges

Buffers useful for carrying out the sample preparation method preferably have pKa values in the range of from about 6.0 to about 9.0. An exemplary pH buffer used for demonstrating utility of the disclosed technique is HEPES (N-2-Hydroxyethylpiperazine-N'-2-Ethane Sulfonic Acid), which has a pKa of 7.55 at 20° C., and which has its strongest buffer capacity in the range of from pH 6.8 to pH 8.2. Of course, success of the technique is not limited by the use of any particular pH buffer.

According to a preferred method, sample preparation is carried out in a multistep procedure. A biological sample, optionally contained in a liquid transport medium, is first combined with an aliquot of a concentrated alkaline reagent to effect cell lysis and denature DNA. This alkaline treatment can be conducted for a period of time between one second and one hour, and optionally can be conducted at elevated temperature. Following the treatment period, the alkaline mixture is combined with a pH buffer, a detergent, and reagents to facilitate capture of nucleic acids onto a solid support. Optionally, these different components can be combined with the alkaline mixture in a specified order (e.g., pH buffer/detergent/target capture reagents; or pH buffer/target capture reagents/detergent). Optionally, the pH buffer and detergent are combined with each other and delivered as a single reagent, followed by delivery of the target capture reagent. Optionally, all three different components are first combined with each other, and then delivered to the alkaline mixture (i.e., the combination of the biological sample and alkaline reagent) as a single reagent. The result of combining the first liquid composition with the pH buffer, detergent, and target capture reagents is a second liquid composition having a pH below pH 9.5.

Preferably, a pH buffered detergent reagent that includes solid support beads or particles that capture nucleic acids, additionally includes one or more immobilizable or immobilized oligonucleotides. Optionally, the solid support displays or harbors bound (e.g., covalently bound) oligonucleotides that participate in capture of nucleic acids from the surrounding solution phase. Use of a single reagent that includes each of the pH buffer, the detergent and the solid support can simplify the reagent addition steps, thereby adapting the method to automation by the use of robotic pipettors or fluid handling devices. Excellent results have been achieved using pH buffered detergent reagents that include solid support beads, where concentrations of the pH buffer fall in the range of from about 200 mM to about 1.0 M, which produced final pH buffer concentrations (i.e., after combining the pH buffered detergent and capture reagent with the biological sample) in the range of from about 200 mM to about 600 mM, more preferably 300 mM to 500 mM, and still more preferably about 400 mM. Of course, the amount of added pH buffer can be adjusted to bring the final pH of the mixture into one of the ranges specified herein.

Certain pH ranges are preferred for isolating nucleic acids in accordance with the disclosed technique. Preferably, the liquid composition that results from combining a biological sample and an alkaline composition (sometimes referred to herein as the "first" liquid composition) has a pH in the range of from pH 12.0 to pH 13.5, still more preferably in the range of from pH 12.5 to pH 13.2, or yet still more preferably in the range of from pH 12.8 to pH 13.1. The added alkaline composition preferably includes a strong base in an aqueous solution. Those having an ordinary level of skill in the art will understand that a strong base is fully ionic, and can dissociate completely in aqueous solution to yield hydroxide ions. Mixing the first liquid composition with a pH buffer, a detergent, and target capture reagents (e.g., including magnetically attractable beads optionally having a polynucleotide immobilized thereon) results in a liquid composition (sometimes referred to herein as the "second" liquid composition) having a pH lower than pH 9.5. More preferably, the second liquid composition has a pH in the range of from pH 7.0 to pH 9.5, still more preferably in the range of from pH 7.4 to pH 9.0, and yet still more preferably in the range of from pH 7.6 to pH 8.8.

Treatment Methods—Alkaline and Detergent Conditions

In a preferred embodiment, a first liquid composition that includes the combination of a biological sample and an alkaline composition is mixed with each of a pH buffer and a detergent, and optionally target capture reagents, to result in a second liquid composition. The second liquid composition is mixed and preferably allowed to incubate with an immobilized capture probe, and optionally also a soluble capture probe capable of forming a bridge between an immobilized probe and a target nucleic acid of interest. As the method is typically practiced, the alkaline composition and the biological sample are first combined in a tube or other reaction vessel. For example, the alkaline composition can be added to a tube or other reaction vessel that already contains the biological sample. Each of the pH buffer, the detergent, and the target capture reagents can then be mixed with the first liquid composition to create the second liquid composition. In a preferred embodiment, the pH buffer, detergent, and magnetically attractable beads displaying an immobilized polynucleotide are delivered to the first liquid composition by a single reagent addition. In a highly preferred embodiment, the target capture reagents include a soluble capture probe that is partially complementary to the immobilized polynucleotide of the magnetically attractable beads.

Substances which may be used as the alkaline composition to effect cellular lysis and denaturation of nucleic acids may be any solid, liquid or gaseous agent which creates a strong alkaline solution when dissolved in aqueous solution. Strong bases are highly preferred for use as alkaline compositions (sometimes referred to herein as "alkaline hydroxides"). Examples of preferred alkaline hydroxides that can be used to carry out the sample preparation method include sodium hydroxide (NaOH), lithium hydroxide (LiOH), potassium hydroxide (KOH), and the like. Although it is contemplated that solid alkaline compositions can be combined with the biological sample, preferred alkaline compositions include a strong base in aqueous solution.

Alkaline conditions in the first liquid composition resulting from combining the biological sample and alkaline composition can be neutralized by addition of a pH buffer to result in a second liquid composition having a pH lower than pH 9.5. The second liquid composition optionally further includes a detergent and target capture reagents (e.g., magnetically attractable beads having a polynucleotide immobilized thereon). The pH buffer, detergent, and target capture reagents optionally can be combined prior to mixing with the first liquid composition.

Preferred Detergents

Detergents that can be used in connection with the disclosed sample preparation technique include anionic detergents, non-ionic detergents, zwitterionic detergents, or cationic detergents. Of these, the anionic and non-ionic detergents are the most preferred. The final detergent concentration in the second liquid composition (i.e., resulting from the aggregated combination of the biological sample, the alkaline composition, and the pH buffered detergent and capture reagent) is preferably between 0.01% (w/v) and 5.0% (w/v), more preferably in the concentration range of between 1.0% (w/v) to 2.0% (w/v), an yet still more preferably in the concentration range of from 1.2% (w/v) to 1.8% (w/v). Strong anionic detergents, including sulfates of alkyl alcohols and N-acyl-amino acids are highly preferred. While the precise nature of the detergent used for conducting the sample preparation procedure is not believed critical, examples of particularly preferred detergents include lithium lauryl sulfate (LLS), and sodium dodecyl sulfate (SDS).

Treatment Period

In a preferred embodiment, a biological sample is combined in a tube or reaction vessel with an alkaline composition (e.g., a strong base in an aqueous solution) to result in a first liquid composition. Optionally, the first liquid composition can be agitated to ensure homogeneity. Advantageously, denatured DNA is stable under the strongly alkaline conditions of the first liquid composition, which denature nucleases that may be present in the first liquid composition. After a period of from about one second to about one hour, the first liquid composition is mixed with each of a pH buffer, a detergent, and reagents for target capture of DNA (e.g., magnetic beads, optionally including a polynucleotide immobilized thereon) to result in a second liquid composition. Optionally, the pH buffer and detergent are first combined with each other before addition to the first liquid composition. Optionally, the pH buffer, the detergent, and the target capture reagents are combined before addition to the first liquid composition. After a period of from one second to one hour, DNA can be isolated from the second liquid composition. This can involve separating or isolating a solid support having DNA captured thereon. Optionally, this isolating step can involve washing the solid support with a wash buffer that permits captured DNA to remain immobilized to the solid support while further removing non-immobilized components of the second liquid composition. To facilitate laboratory productivity, the length of time during which the target-capture step is performed is desirably no longer than necessary. However, because DNA liberated from the biological sample will be stable in the second liquid composition (e.g., due to the presence of the detergent), allowing the mixtures to stand for at least a few hours is not believed harmful to the target DNA.

Plastic Containers Disposed in an Automated Analyzer

The sample preparation method preferably is carried out in a disposable reaction vessel, such as a plastic tube, or a disposable unit comprising a plurality of tubes held in a spaced-apart configuration. For example, the disposable reaction vessel containing a biological sample is preferably positioned within an automated instrument or analytical device at the time that the alkaline composition (e.g., an alkaline hydroxide solution) is added to create a first liquid composition. The addition step is preferably carried out by an automated or robotic pipetting device. The alkaline composition added to the biological sample is sufficient for lysing or disrupting biological membranes, such as cell walls of bacteria (e.g., Gram-positive bacteria), cell membranes, viral envelopes, and the like, even in the absence of added detergent. In a highly preferred embodiment, the disposable reaction vessel is loaded into the analytical device, and an automated or robotic pipetting device adds to the vessel an aliquot of the biological sample and an aliquot of the alkaline composition. An automated or robotic pipetting device next can add to the first liquid composition contained in the disposable reaction vessel each of: a pH buffer, a detergent, and target capture reagents (e.g., magnetically attractable beads). Optionally, the pH buffer, detergent, and the target capture reagents can all be added to the first liquid composition in a single reagent addition to result in creation of the second liquid composition. The contents of the tube can then be agitated to ensure complete mixing, and the mixed sample incubated at a temperature and for a period of time sufficient to permit capture of the liberated polynucleotides. By this approach, DNA can be isolated even from bacterial cells that are difficult to lyse. However, RNA is substantially degraded. Accordingly, substantially RNA-free DNA can be isolated by this sample preparation technique. Given the chemical stability of DNA, and the fact that nuclease enzymes are substantially inactivated by the harsh alkaline and detergent conditions of the first and second liquid compositions, there is no substantial chemical degradation that is known to occur by extended or variable periods of standing, as may occur when different analytical protocols are executed on the automated analyzer in a single daily cycle of laboratory testing. Finally, plastic material of the disposable reaction vessel must be chemically resistant to each mixture that is to be contained therein.

Target Capture—Methods and Oligonucleotides

The disclosed sample preparation method has particular value when including a target capture procedure that enriches the sample for nucleic acids. Separate preferred embodiments rely on non-specific target capture (i.e., where nucleic acids are captured in a manner substantially independent of the base sequence of the nucleic acids), and on sequence-specific target capture. Either or both of these methods can employ an immobilizable or immobilized capture oligonucleotide, and each method can capture single-stranded (e.g., "denatured") DNA.

Preferred capture oligonucleotides include a first sequence that is complementary to a polynucleotide containing a target sequence that is to be amplified, covalently attached to a second sequence (e.g., a "tail" sequence) that serves as a target for immobilization on a solid support. Any backbone to link the base sequence of a capture oligonucleotide may be used. In certain preferred embodiments, the capture oligonucleotide includes a DNA backbone. In other preferred embodiments, the capture oligonucleotide includes at least one sugar-phosphate backbone analog. For example, there can be at least one methoxy linkage in the backbone. The tail sequence, which is preferably at the 3' end of a capture oligonucleotide, is used to hybridize to a complementary base sequence to provide a means for capturing the hybridized target nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide optionally can include a first sequence that specifically binds a target polynucleotide, and a second sequence that specifically binds an oligo(dT) stretch immobilized to a solid support.

In some embodiments, an assay for detecting nucleic acid sequences in a biological sample includes the steps of capturing the target nucleic acid using the capture oligonucleotide, amplifying the captured target region using at least one, and preferably at least two amplification oligonucleotides, or at least two primers, and detecting the amplified nucleic acid by first hybridizing an oligonucleotide probe to a sequence contained in the amplified nucleic acid. A signal resulting from the bound probe preferably is detected. Optionally, the probe harbors a detectable label (e.g., a fluorescent label), or includes a stretch of nucleotides at its 5'end (e.g., a probe participating in an invasive cleavage assay).

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices, beads or particles free in solution (e.g., nitrocellulose, nylon, glass, polyacrylate, mixed polymers, polystyrene, silane polypropylene and, preferably, magnetically attractable beads or particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size±about 5%).

Retrieving the target nucleic acid:capture oligonucleotide:immobilized probe complex effectively concentrates the target nucleic acid, relative to its concentration in the biological sample, and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may contain mismatches to the above-indicated sequences, as long as the mismatched sequences hybridize to the nucleic acid containing the sequence that is to be amplified.

Previous testing has demonstrated that poor target capture results can occur when the pH of the second liquid composition exceeds pH 9.5. Accordingly, target capture can take place in a liquid composition having a pH that is lower than pH 9.5.

Useful Amplification Methods

Amplification methods useful in connection with the sample preparation techniques include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. Nos. 4,965,188, 5,455,166, 5,472, 840 and Lizardi et al., BioTechnology 6:1197 (1988). The disclosures of these documents which describe how to perform nucleic acid amplification reactions are hereby incorporated by reference.

In some embodiments, target nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

In some embodiments, target nucleic acid sequences are amplified by PCR. Optionally, detection of amplification products can take place as the reaction is occurring (i.e., so-called "real time PCR"). Commonly, a fluorescent signal that increases with time or cycle number indicates the presence of amplification products in the reaction. Procedures used in the Examples described below employed the PCR technique.

Kits

The disclosure also embraces kits that can be used for carrying out the disclosed sample preparation procedures. Kits typically will include in separate vials or containers: an alkaline composition (e.g., a strong base), a pH buffer, a detergent, and target capture reagents. In certain embodiments, one or more of these reagents is a dry, lyophilized, or semi-solid composition which can be reconstituted with a liquid component, such as water, prior to use. In certain embodiments, the alkaline composition requires reconstitution with a liquid agent prior to use. In other embodiments, the alkaline composition is packaged in the kit as a liquid composition.

The following Examples describe development of a sample preparation technique useful for isolating nucleic acids from a range of bacteria, and provide reasons why certain methods were considered superior to others. Workflows employing initial contact between a biological sample undergoing testing and a lysis reagent that included a detergent and either strong base at high pH, or a pH buffered detergent solution at substantially neutral pH surprisingly did not give the best results when isolating nucleic acids from organisms that were considered difficult to lyse. Most testing described below was conducted using an automated instrument that performed steps for sample processing and real time nucleic acid amplification and detection. In some instances, the automated instrument was used only for sample processing (e.g., isolation of DNA from a biological sample), and nucleic acid amplification was conducted on a different instrument. In all cases, detection of target organisms using nucleic acid amplification assays was evidence of efficient lysis of the target organism in the biological sample.

Example 1 demonstrates that a lysis protocol employing the combination of a strong base and a detergent gave good results with a prototype real time multiplex assay that detected methicillin-resistant *S. aureus* (MRSA). Results indicated 100% detection of the target organism at an input level of 1,000 CFU/ml.

Example 1

Demonstrating Lysis of Methicillin-Resistant *Staphylococcus aureus* (MRSA)

Efficiency of bacterial cell lysis and nucleic acid isolation was judged using a prototype real time assay for detecting *S. aureus* or MRSA. The assay amplified four target nucleic acid sequences in a multiplex PCR-format, where one of the targets was an internal control (IC) that did not depend on the presence of the target organism. Three nucleic acid targets used for detecting MRSA were: a *S. aureus*-specific target; mecA or mecC (i.e., indicating drug resistance); and a "junction" sequence indicating insertion of a movable drug resistance element into the *S. aureus* chromosome. Positive MRSA calls were made when each of the *S. aureus* marker, the junction marker, and the mecA or mecC sequences were all detected.

The procedure for isolating nucleic acids from the target organism was divided into three parts: sample lysis; target capture; and a step for washing the captured nucleic acids. Tubes containing samples of MRSA bacteria (strain ATCC BAA-41) at 100 CFU/ml-10,000 CFU/ml in modified Liquid Amies transport medium (Copan Diagnostics Inc.; Corona, CA). This detergent-free transport medium, which preserves viability of bacterial cells for subsequent culture or propagation, includes NaCl, KCl, $CaCl_2$, $MgCl_2$, monopotassium phosphate, disodium phosphate, and sodium thioglycollate in an aqueous solution. Sample lysis was effected by combining 126 µl of a lysis reagent ("LR-A") with 300 µl of the liquid containing the biological sample to be tested, thereby resulting in a first liquid composition. The LR-A used in the procedure was a detergent-free aqueous solution that included 0.4 N LiOH, 8% LLS, 2% TRITON X-100, and 0.05% of an anti-foaming reagent. TRITON X-100 was included in the LR-A reagent to aid in processing any samples containing added mucin (e.g., to model nasal swab samples). The resulting alkaline mixtures were incubated for 10 minutes at 43° C. to model the workflow in an automated sample processing instrument. The incubation step is optional, and so can be omitted. Capture of nucleic acid targets onto solid supports involved mixing 450 µl of a target capture reagent with the first liquid composition to give a second liquid composition. The target capture reagent was an aqueous solution that included LiOH, HEPES buffer, lithium lauryl sulfate, succinic acid, an anti-foaming agent, poly(dT) 14 magnetic beads, and a target capture oligonucleotide having a poly(dA)$_{30}$ tail at its 3'-end. Non-specific capture oligonucleotides used in the procedure were in accordance with the description contained in U.S. Pat. No. 9,051,601, the disclosure of which is incorporated by reference herein. Beads harboring captured nucleic acids were pulled to the sides of the tubes under the influence of a magnetic field, liquid was aspirated, and the beads washed using a wash buffer that included HEPES (pH 7.5), EDTA, NaCl, and sodium lauryl sulfate. After isolating and washing the magnetic beads to remove non-immobilized materials, nucleic acids captured on the beads served as templates in the real time PCR multiplex assay.

Table 1 presents results confirming that MRSA bacteria were easily detected when the sample included at least 1,000 CFU/ml of the target organism. Indeed, the evidence showed that the limit of detection (LoD) for the assay was between 300 CFU/ml and 1,000 CFU/ml.

TABLE 1

Scoring MRSA Detection

| MRSA Input (CFU/ml) | Junction Target | | mecA/mecC Targets | | S. aureus Target | |
|---|---|---|---|---|---|---|
| | Mean Ct | Positivity | Mean Ct | Positivity | Mean Ct | Positivity |
| 100 CFU/ml | 39.4 | 4/8 | 41.1 | 7/8 | 40.4 | 6/8 |
| 300 CFU/ml | 38.4 | 8/8 | 39.4 | 7/8 | 39.4 | 8/8 |
| 1,000 CFU/ml | 35.9 | 8/8 | 37.3 | 8/8 | 37.3 | 8/8 |
| 3,000 CFU/ml | 34.5 | 8/8 | 35.9 | 8/8 | 35.8 | 8/8 |
| 10,000 CFU/ml | 32.7 | 8/8 | 34.1 | 8/8 | 34.1 | 8/8 |

Example 2 describes use of the lysis reagent and conditions from Example 1 for isolating nucleic acids from a different organism. As indicated below, C. difficile bacteria did not lyse efficiently to yield amplifiable nucleic acids by this approach.

Example 2

Reagent that Lyses S. aureus does not Efficiently Lyse C. difficile

Lysis and target capture reagents and conditions from Example 1 were next used for isolating nucleic acids from C. difficile bacteria. The isolated nucleic acids served as templates in a prototype real time amplified assay for detecting C. difficile bacteria, where results from the assay indicated success of the sample processing procedure. "Up-front" sample processing was tested by comparing results from the prototype C. difficile assay, where the variable was the composition of the liquid reagent used for transporting the biological sample. In one instance, the sample transport tube contained 2.9 ml of a phosphate-buffered (pH 6.6 to pH 6.8) solution that included 3% (w/v) lithium lauryl sulfate. In addition to promoting cell lysis, this solution (specimen transport medium, or "STM") protects released nucleic acids by inhibiting the activity of nuclease enzymes that may be present in the sample. Alternatively, STM was substituted by a lysis reagent that was 0.4 N LiOH and 10% LLS.

Results of the amplification reaction confirmed that both sample processing procedures gave good final results from the amplification and detection assays. Regardless of whether samples of C. difficile bacteria were introduced into tubes containing STM or lysis reagent, each condition correctly yielded 3/3 positive results. There was, however, a key difference in the nature of the measurements leading to these conclusions. Whereas the sample processed using lysis buffer gave a Ct value of about 22.2, the sample processed using STM gave a Ct value of about 26.7. This substantial difference in the time of emergence during the real time amplification indicated that at least 10 fold more DNA was liberated when the biological sample was contained in the alkaline detergent lysis reagent rather than STM. Practical considerations made it undesirable to include strong alkali in the same tube that would be used for sample collection. This prompted efforts to develop a general purpose sample preparation technique that could be used for isolating nucleic acid from S. aureus, C. difficile, and other bacteria also considered difficult to lyse.

Example 3 describes procedures used for exploring the benefits of increasing the concentration of strong base in the lysis reagent. The experiment described below particularly compared the effect of including or omitting detergent in the alkaline lysis reagent. Surprisingly, the presence of detergent actually reduced assay sensitivity when the concentration of strong base was increased.

Example 3

Detergent in the Lysis Reagent Reduces Assay Sensitivity

The effect of increasing the concentration of strong base in the lysis buffer was assessed using a modified version of the procedure described under Example 1. The effect of including or omitting detergent in the lysis reagent also was assessed in the same procedure. All samples, which included either 300 or 1,000 CFU/ml of MRSA bacteria (strain ATCC BAA-41) in Liquid Amies transport media, further included 0.25% mucin to simulate nasal swab specimens. Again, sample processing involved combining 300 µl of liquid containing the biological sample with 126 µl of lysis reagent. Lysis reagent used in this procedure was either 1.35 N LiOH, or the combination of 1.35 N LiOH and 2% TRITON X-100. Following a brief incubation, 450 µl of the target capture reagent (e.g., pH buffered detergent solution containing target capture reagents) was added to neutralize the alkaline mixture and facilitate immobilization or capture of nucleic acids onto the solid support beads. All testing was carried out in replicates of 20.

Table 2 presents results confirming the finding that samples including MRSA at levels of at least 1,000 CFU/ml yielded positive detection of all three targets needed to make the MRSA identification. The table further includes results for positive detection of the internal control (IC), which does not depend on successful bacterial lysis to generate a positive result. Indeed, the IC template nucleic acid that was amplified and detected in the MRSA assay was always added as a component of the pH buffered detergent solution containing target capture reagents. Significantly, increasing the strong base concentration from 0.4 N to 1.35 N increased the efficiency of bacterial lysis to the point where each target could be detected in the amplified assay at an MRSA input level of 300 CFU/ml. Thus, the increased concentration of strong base enhanced bacterial lysis, even in the absence of any detergent. Surprisingly, the results in Table 2 also indicated that the presence of detergent in the alkaline lysis reagent had a detrimental effect evidenced by decreased positivity of all targets at the MRSA input level of 300 CFU/ml. Additional investigations conducted using increasing concentrations of strong base and LLS as the detergent revealed formation of a very thick mixture containing a precipitate that rendered the composition unusable as a lysis reagent when the concentration of strong base rose to 2.5 N.

TABLE 2

Detergent Decreases Efficiency of Bacterial Lysis

| Lysis Reagent | MRSA Input (CFU/ml) | Junction Target Positivity | mecA/mecC Target Positivity | S. aureus Target Positivity | IC Positivity |
|---|---|---|---|---|---|
| 1.35N LiOH | 300 | 100% | 100% | 100% | 100% |
| | 1,000 | 100% | 100% | 100% | 100% |
| 1.35N LiOH and 2% TRITON-X100 | 300 | 85% | 95% | 85% | 100% |
| | 1,000 | 100% | 100% | 100% | 100% |

The findings presented under Example 3 indicated that elevated concentrations of strong base were not appropriate for use in combination with detergents. More particularly, lysis reagent containing the combination of 1.35 N LiOH and 2% TRITON X-100 did not yield the same high level of sensitivity that was achieved when detergent was omitted. Indeed, use of the strong base as a lysis reagent in the absence of pH buffer and detergent permitted 100% detection of 300 CFU/ml, a level of sensitivity better than that achieved using the LR-A of Example 1. Moreover, further increasing the concentration of strong base to 2.5 N undesirably caused formation of a precipitate in lysis reagents including LLS at a level of at least 8%.

Example 4 describes procedures illustrating useful pH conditions for isolation of nucleic acids from *C. difficile* bacteria. As described elsewhere herein, the pH conditions demonstrated as useful in this Example fell in the range of desired pH conditions for lysing cells and capturing nucleic acids onto solid supports.

Example 4

Demonstration of pH Conditions for Bacterial Cell Lysis and Capture of Nucleic Acids Readings for pH were determined at each of three steps where sample transport, bacterial lysis, and target capture took place. It was determined that the biological sample in STM had pH 6.6, as expected. Combining 300 μl of biological sample with 126 μl of LiOH solution having a concentration falling in the range of from 1.325 N to 2.5 N yielded pH of about pH 12.95 to about pH 12.99. Mixing this alkaline sample with 450 μl of target capture reagent yielded a pH falling in the range of from pH 7.91 to pH 8.75. Captured and washed nucleic acids were subjected to nucleic acid amplification and detection using a prototype amplified assay for detecting *C. difficile* bacteria. Efficiency of lysis and target capture were assessed using results from the amplified assay.

Results from the procedure indicated that bacterial cell lysis and target capture were efficient in nearly all instances. Only when the pH of the second liquid composition resulting from mixing the base-treated biological sample with the target capture reagent (e.g., the pH buffered detergent solution) was pH 11.81 (e.g., resulting from use of inadequately buffered target capture reagent) was the target capture inefficient. All of these results were consistent with preferred ranges of pH 12.0 to pH 13.5 for lysing cells and denaturing DNA, and less than pH 9.5 (e.g., pH 7.9 to pH 9.2) for permitting hybridization-based target capture.

Example 5 describes results indicating that detergent can be required for best results in sample preparation procedures employing strong base at certain concentrations.

Example 5

Reducing Detergent Concentration During Lysis Step Compromises Results

A procedure essentially as described under Example 1 was followed, except that the concentration of detergent in the lysis reagent varied from 0% (w/v) up to 10% (w/v), instead of being fixed at 8% (w/v). All tested lysis reagents included 0.4 N LiOH. All trials were conducted using a fixed MRSA level of 1,000 CFU/ml, and 0.25% mucin in the modified Liquid Amies transport medium to simulate a sample that included nasal fluid. Positivity for detection of each of the four amplified targets was assessed and compared at each detergent level.

Results presented in Table 3 unexpectedly demonstrated that the different amplified targets were differentially sensitive to the amount of detergent used during the sample lysis procedure. As well, eliminating detergent completely gave very poor results. These findings suggested that the combination of detergent and alkali was required for efficient lysis of MRSA bacteria at the tested level of strong base. As indicated elsewhere herein, the conditions that efficiently lysed one type of bacteria did not efficiently lyse all other types of bacteria. Thus, it was of interest to develop a single lysis reagent that could be used on an automated sample preparation platform for lysing all types of bacteria.

TABLE 3

Detergent Concentration in Lysis Reagent Affects Efficiency of Target Detection

| LLS Conc. | Junction Target | mecA/mecC Target | *S. aureus* Target | IC |
|---|---|---|---|---|
| 10% | 60% | 100% | 60% | 100% |
| 6% | 60% | 100% | 40% | 100% |
| 4% | 80% | 100% | 40% | 100% |
| 0% | 20% | 80% | 0% | 100% |

Example 6 demonstrates how a sample preparation technique employing contact of a biological sample with an alkaline composition that lacked a detergent and pH buffer, followed by neutralizing in the presence of detergent and target capture reagents could improve results in a prototype amplified assay for detecting Group B *Streptococcus* (GBS) bacteria. The GBS bacteria are another group of bacteria that, like *S. aureus* and *C. difficile* are known to be difficult to lyse. *Streptococcus agalactiae* served as a representative of the GBS bacteria in this Example. Comparative results presented below confirmed that superior results could be obtained using the technique disclosed herein.

Example 6

Detection of GBS Bacteria Dramatically Improved by Sample Preparation Technique

A prototype assay for detecting nucleic acids of GBS bacteria was used to compare effectiveness of two different sample preparation techniques. The two methods employed substantially identical reagents, but differed in procedural steps used for processing samples, with very different results. A first method involved combining the biological sample and a pH buffered detergent solution that included target capture reagents (e.g., magnetic beads displaying an immobilized oligonucleotide, etc.) to create a first liquid composition having a pH falling in the range of from pH 6.5 to pH 8.0. Thereafter, an aliquot of a strong base solution (1.68 N LiOH) was mixed with the first liquid composition to create a second liquid composition having a pH less than pH 9.5 (e.g., pH 8.2 to pH 9.2) and providing conditions appropriate for capture of nucleic acids by immobilization to a solid support. Captured nucleic acids were purified by washing the solid support with a wash buffer. A second method involved combining the biological sample with an aliquot of an alkaline composition (1.68 N LiOH) that lyses cells and denatures nucleic acids to create a first liquid composition. The alkaline composition that was mixed with the biological sample was free of detergents and pH buffers, and the pH of the first liquid composition was greater than pH 12.5 (e.g., pH 12.5 to pH 13.2). Thereafter, an aliquot of a pH buffered detergent solution that included target capture reagents (e.g., magnetic beads displaying an immobilized oligonucleotide, etc.) was mixed with the first liquid composition to create a second liquid composition having a pH less than pH 9.5 (e.g., pH 7.8 to pH 8.9) and providing conditions appropriate for capture of nucleic acids by immobilization to a solid support. Captured nucleic acids were purified by washing the solid support with a wash buffer.

While the first method described in this Example was useful for isolating both RNA and DNA, the second method was useful for isolating DNA and substantially eliminating RNA from the finally purified nucleic acid composition. Testing carried out using a known input level of an RNA viral target prepared by the two different methods illustrated this fact. More specifically, quantitative real time PCR amplification and detection revealed that the difference in the time of emergence for the two run curves was about 24 Ct intervals. This meant that the number of copies of the RNA target was reduced by about 16 million fold using the second sample method.

Results presented in Table 4 confirmed that the sample preparation technique employing the alkaline composition (strong base without pH buffer or detergent) for lysing bacteria gave superior results. More particularly, the limit of detection was determined to be about 39 CFU/ml with this technique. Conversely, use of an alkaline shock technique for lysing GBS bacteria gave a limit of detection of 1,416 CFU/ml. Again, first treating with strong base followed by neutralizing in the presence of pH buffer, detergent, and target capture reagents gave superior results in the automated sample preparation workflow.

TABLE 4

Efficient Lysis of GBS Bacteria
by an Alkaline Composition Followed by Neutralizing
in the Presence of Detergent Yields Superior Results

| Input GBS Level (CFU/ml) | Method 1 Positivity | Method 2 Positivity |
| --- | --- | --- |
| 0 | 0% | 0% |
| 30 | 14.3% | 81.0% |
| 100 | 38.1% | 100% |
| 300 | 52.4% | 100% |
| 1,000 | 90.5% | 100% |
| 3,000 | 100% | 100% |

Significantly, the second of the two sample preparation methods used in Example 6 also was used for obtaining efficient lysis and capture of nucleic acids from biological samples that included either *S. aureus* or *C. difficile* bacteria.

As used herein, a first liquid composition can be said to be "substantially free of detergents" when the detergent concentration is less than 0.001% (w/v). Biological samples stored in modified Liquid Amies transport medium and then combined or mixed with an alkaline composition lacking detergent yielded first liquid compositions that were completely free of detergents, and gave excellent results in the DNA isolation procedure.

Advantageously, bacteria transported in media lacking detergent remained viable and could be cultured for species verification or typing using conventional microbiological techniques. Thus, a single biological sample could be used for both molecular analysis and microbiological analysis. Clearly though, the presence of detergent in the first liquid composition did not compromise the ability to achieve good results with the DNA isolation method. Indeed, the first liquid composition that resulted from combining the biological sample (stored in STM) and the alkaline composition in the preceding Example had a detergent concentration of about 2% (w/v), and also gave excellent results, as indicated by efficient detection of GBS sequences in the PCR protocol.

The invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of processing a biological sample, the method comprising the steps of:
   (a) mixing the biological sample with an alkaline composition that lyses cells and denatures DNA to create a first liquid composition,
      wherein the first liquid composition has a pH in the range of from pH 12.0 to pH 13.5, and
      wherein the first liquid composition is free of detergents;
   (b) mixing the first liquid composition with a pH buffered detergent reagent to create a second liquid composition having a pH lower than pH 9.5,
      wherein the pH buffered detergent reagent comprises a pH buffer, a detergent, and a solid support particle that captures DNA; and
   (c) isolating the solid support particle, and any DNA captured thereon, from the second liquid composition.

2. The method of claim 1, wherein the biological sample comprises viable bacterial cells, and wherein the method further comprises the step of culturing the viable bacterial cells to increase the number of bacterial cells.

3. The method of claim 1, wherein the second liquid composition has a pH in the range of from pH 8.0 to pH 9.2.

4. The method of claim 1, wherein each of steps (a)-(c) is conducted onboard an automated instrument that comprises a robotic fluid transfer device.

5. The method of claim 4, further comprising the step of (d) performing an in vitro nucleic acid amplification reaction using DNA isolated in step (c) as templates, and detecting products of the in vitro nucleic acid amplification reaction.

6. The method of claim 5, wherein detecting products of the in vitro nucleic acid amplification reaction indicates the presence of a species of Gram-positive bacteria in the biological sample.

7. The method of claim 5, wherein step (d) is carried out onboard the automated instrument.

8. The method of claim 4, wherein step (a) comprises combining the biological sample and the alkaline composition in a reaction vessel to create the first liquid composition, wherein step (b) comprises adding the pH buffered detergent reagent to the reaction vessel containing the first liquid composition to create the second liquid composition, and wherein each of steps (a) and (b) is performed using the robotic fluid transfer device of the automated instrument.

9. The method of claim 8, wherein the automated instrument further comprises a transport mechanism that moves the reaction vessel from one position within the automated instrument to a different position within the automated instrument.

10. The method of claim 9, wherein after step (b) and before step (c) there is the step of incubating the first liquid composition for a period of time between 1 minute and 10 minutes.

11. The method of claim 10, wherein the incubating step comprises heating the first liquid composition.

12. The method of claim 10, wherein the incubating step comprises transporting the reaction vessel from a first position in the automated instrument to a second position in the automated instrument, and wherein the second position in the automated instrument is at a temperature higher than the temperature at the first position in the automated instrument.

13. The method of claim 1, wherein the solid support particle comprises a magnetically attractable particle.

14. The method of claim 1, wherein the solid support particle in step (b) is a solid support particle that captures DNA independent of base sequence, and wherein step (c) comprises washing the solid support particle to remove any material not immobilized thereon, and then retaining the solid support particle after washing, whereby captured DNA is isolated.

15. The method of claim 1, wherein the alkaline composition comprises a strong base in aqueous solution at a concentration of from 0.1 N to 2.2 N.

16. The method of claim 15, wherein the pH of the first liquid composition is in the range of from pH 12.5 to pH 13.2.

17. The method of claim 15, wherein the pH of the second liquid composition is in the range of from pH 7.6 to pH 8.8.

18. The method of claim 15, wherein the alkaline composition comprises the strong base at a concentration of from 1.0 N to 1.7 N.

19. The method of claim 15, wherein the strong base is selected from the group consisting of NaOH, KOH, and LiOH.

20. The method of claim 1, wherein all steps are carried out under automated process control.

\* \* \* \* \*